United States Patent [19]

Wong et al.

[11] Patent Number: 5,561,117
[45] Date of Patent: Oct. 1, 1996

[54] BRIDGED BIS-ARYL CARBINOL DERIVATIVES, COMPOSITIONS AND METHODS OF USE

[75] Inventors: Jesse K. Wong, Union; John J. Piwinski, Parsippany, both of N.J.

[73] Assignee: Schering Corporation, Kenilworth, N.J.

[21] Appl. No.: 307,714

[22] PCT Filed: Mar. 24, 1993

[86] PCT No.: PCT/US93/02418

§ 371 Date: Sep. 23, 1994

§ 102(e) Date: Sep. 23, 1994

[87] PCT Pub. No.: WO93/20080

PCT Pub. Date: Oct. 14, 1993

Related U.S. Application Data

[63] Continuation-in-part of Ser. No. 858,915, Mar. 27, 1992, abandoned.

[51] Int. Cl.$^6$ .................. A61K 31/44; C07D 221/06
[52] U.S. Cl. ............... 514/291; 514/290; 546/80; 546/89; 546/93
[58] Field of Search ................. 546/80, 89, 93; 514/290, 291

[56] References Cited

U.S. PATENT DOCUMENTS

| | | | |
|---|---|---|---|
| 2,739,968 | 3/1956 | Sperber et al. | 544/130 |
| 2,898,339 | 8/1959 | Wheeler et al. | 546/194 |
| 3,325,501 | 6/1967 | Ettinsen | 514/849 |
| 3,326,924 | 6/1967 | Villani | 546/93 |
| 3,717,647 | 2/1973 | Villani | 546/315 |
| 3,803,153 | 4/1974 | Villani | 540/587 |
| 3,803,154 | 4/1974 | Drukker | 514/960 |
| 3,922,276 | 11/1975 | Duncan, Jr. et al. | 546/226 |
| 3,956,296 | 5/1976 | Duncan, Jr. et al. | 544/130 |
| 3,966,944 | 6/1976 | Carter | 514/318 |
| 4,032,642 | 6/1977 | Duncan, Jr. et al. | 514/237.2 |
| 4,105,849 | 8/1978 | Hamilton et al. | 544/129 |
| 4,282,233 | 8/1981 | Villani | 546/93 |
| 4,355,036 | 10/1982 | Villani | 514/316 |
| 4,540,780 | 9/1985 | Downs | 544/129 |
| 4,609,664 | 9/1986 | Hasspacher | 514/324 |
| 4,659,716 | 4/1987 | Villani et al. | 514/290 |
| 4,797,489 | 1/1989 | Abou-Gharbia et al. | 544/331 |
| 4,826,853 | 5/1989 | Piwinski et al. | 514/290 |
| 4,835,157 | 5/1989 | Press et al. | 514/258 |
| 5,089,496 | 2/1992 | Piwinski et al. | 514/253 |
| 5,104,876 | 4/1992 | Piwinski et al. | 514/254 |
| 5,151,423 | 9/1992 | Piwinski et al. | 514/254 |

FOREIGN PATENT DOCUMENTS

| | | |
|---|---|---|
| 638971 | 4/1964 | Belgium . |
| 644121 | 8/1964 | Belgium . |
| 780443 | 11/1986 | Canada . |
| 0042544 | 12/1981 | European Pat. Off. . |
| 81810337 | 3/1982 | European Pat. Off. . |
| 0113226 | 11/1984 | European Pat. Off. . |
| 0235463 | 9/1987 | European Pat. Off. . |
| 0283310 | 9/1988 | European Pat. Off. . |
| 0371805 | 6/1990 | European Pat. Off. . |
| 0385350 | 9/1990 | European Pat. Off. . |
| 17764 | 4/1964 | Ireland . |
| 864458 | 6/1986 | South Africa . |
| 864522 | 6/1986 | South Africa . |
| 8803138 | 5/1988 | WIPO . |
| 8910363 | 11/1989 | WIPO . |
| 8910369 | 11/1989 | WIPO . |
| 9013548 | 11/1990 | WIPO . |
| 9206970 | 4/1992 | WIPO . |

OTHER PUBLICATIONS

Villani et al., Journal of Medicinal Chemistry, vol. 15, No. 7, pp. 750–754 (1972).
Arzn. Forsh 36 1311–1314 (1986).
Galantay et al., Journal of Medicinal Chemistry, vol. 17, No. 12, pp. 1316 to 1327 (1974).
Ohtaka et al., Chem. Pharm. Bull., 35(10)4124–4129 (1982).
Kennis et al., Drug Development Research, 8:133–140 (1986).
Regnier et al., Eur. J. Med. Chem, 22 (1987)243–250.
Nishikawa et al., J. Med. Chem. 1989, 32, 583–593.
Anagnostupolos, Eur. J. Med. Chem. 24 (1989)227–232.
Ohtaka et al., Chem. Pharm. Bull, 35(8)3270–3275 (1987).
Cid et al., Tetrahedron, vol. 44, No. 19, pp. 6197 to 6200 (1988).
Meyer et al., Journal of Medicinal Chemistry, 1989, vol. 32, No. 3, pp. 593–597.
Gubert et al., Azneim–Forsch./Drug Res. 37(II), No. 10 (1987) pp. 1103–1107.
Bickel, Pharmacological Review, 1969, vol. 21, No. 4, pp. 325 & 335–336.
Wade, Jr., Organic Chemistry, 1987, Prentice-Hall Inc., p. 349.

*Primary Examiner*—Ceila Chang
*Attorney, Agent, or Firm*—Henry C. Jeanette

[57] ABSTRACT

The invention is drawn to bridged bis-aryl carbinol compounds of formula (I):

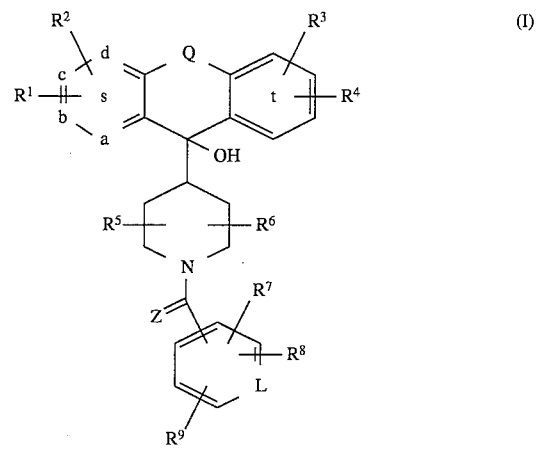

wherein, a, b, c, d, Q, Z, L and $R^1$–$R^9$ are as defined in the specification, their pharmaceutical composition and method of using them in treating asthma, allergy and inflammation.

15 Claims, No Drawings

BRIDGED BIS-ARYL CARBINOL DERIVATIVES, COMPOSITIONS AND METHODS OF USE

The present application is the United States national application corresponding to International Application No. PCT/US 93/02418, filed Mar. 24, 1993 and designating the United States, which PCT application is in turn a continuation-in-part of U.S. application Ser. No. 07/858915, filed Mar. 27, 1992, now abandoned.

BACKGROUND OF THE INVENTION

The present invention relates to bis-aryl carbinol derivatives, pharmaceutical compositions and methods of using such derivatives.

International Publication Number WO 89/10369 discloses compounds of the formula:

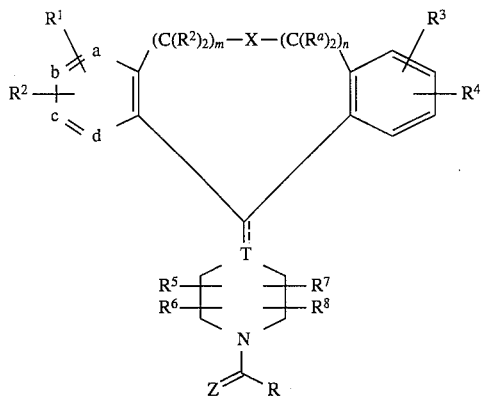

wherein: one of a, b, c and d represents nitrogen or —$NR^{11}$—, wherein $R^{11}$ is, amongst others, $O^-$, and the remaining a, b, c and d groups are CH; T represents carbon or nitrogen, with the dotted line attached to T representing an optional double bond when T is carbon; when m plus n equals 1 or 2, X represents, amongst others, —O— or —$S(O)_e$— wherein e is 0, 1 or 2; when m plus n represents 0, X can be, amongst others, any substituent for m plus n equalling 1, a direct bond or propenylene; when m plus n equals 3 then X equals a direct bond; each $R^a$ may be, amongst others, H; Z represents =O or =S such that when Z is O, R may be, amongst others,

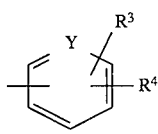

wherein Y is N or $NR^{11}$; when Z represents =S, R represents in addition to the R group above, aryloxy or alkoxy.

WO 89/10369 generically discloses compounds which can have the structure:

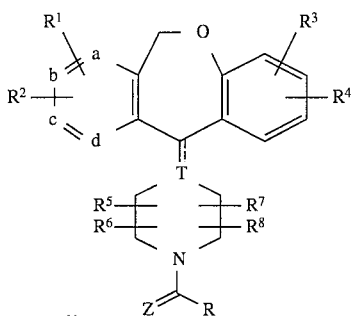

wherein Z can be O and R can be:

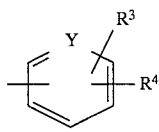

wherein Y can be $NR^{11}$ and $R^{11}$ can be —$O^-$; however, no specific compounds are disclosed with this structure.

U.S. Pat. No. 4,826,853 issued to Piwinski et al. on May 2, 1989 is the priority document for WO 88/03138 which published on May 5, 1988. WO 88/03138 discloses compounds of the formula

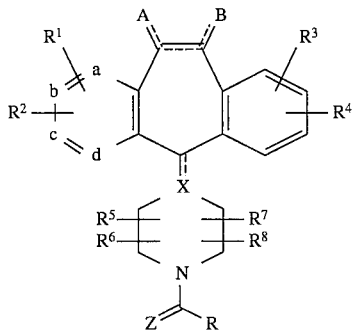

wherein: one of a, b, c and d represents N or $NR^9$ where $R^9$ is, amongst others, O, and the remaining a, b, c and d groups are CH; X represents N or C, which C may contain an optional double bond to carbon atom 11; Z represents O, S or $H_2$ such that when Z is O, R may be, amongst others,

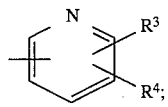

when Z represents S, R represents in addition to the R group above, aryloxy or alkoxy; and when Z represents $H_2$, R can be, amongst others,

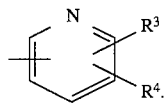

These compounds are disclosed as being useful in the treatment of allergy and inflammation.

In particular, WO88/03138 discloses intermediates having the formulas:

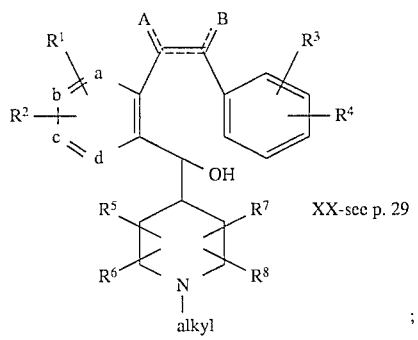

XX-see p. 29

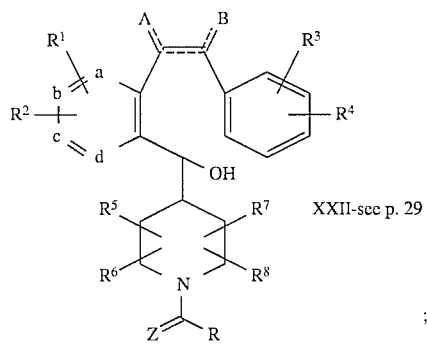

XXII-see p. 29

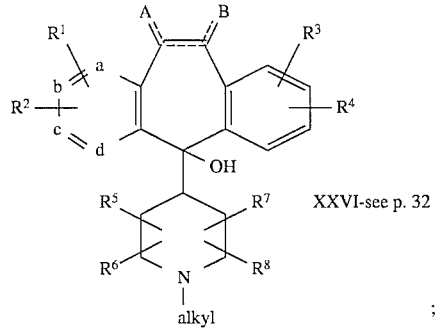

XXVI-see p. 32

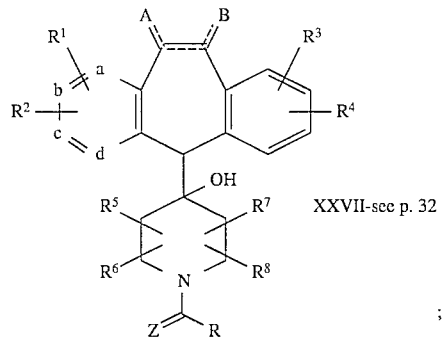

XXVII-see p. 32

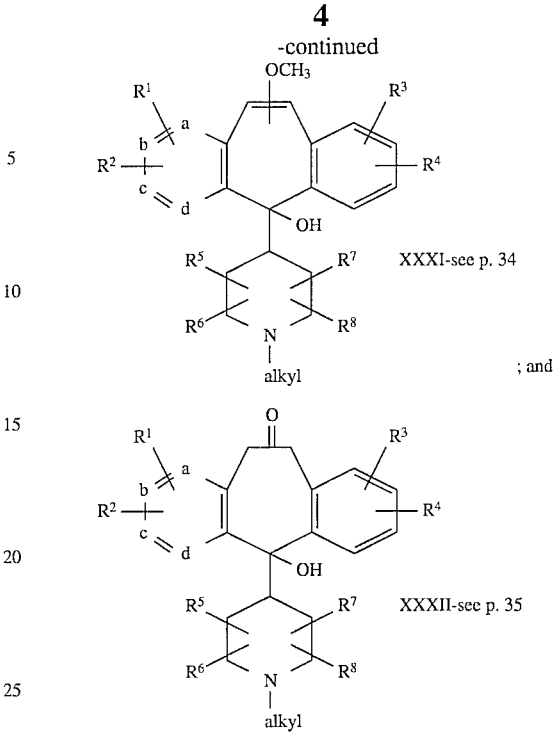

XXXI-see p. 34

; and

XXXII-see p. 35

During the course of research on the compounds disclosed in WO 88/03138, it was generally found that the compounds having a carbonyl group (Z=O) attached to the piperidyl, piperidylidenyl or piperazinyl nitrogen atom were much stronger antagonists of platelet activating factor (PAF) than the compounds having a $CH_2$ group (Z=$H_2$) attached thereto.

WO 90/13548 published on Nov. 15, 1990 on PCT/US90/02251 which was filed on Apr. 30, 1990 and claims priority to U.S. application Ser. No. 345,604 filed May 1, 1989 discloses compounds similar in structure to the compounds disclosed in WO 88/03138 with the difference being that the R group represents an N-oxide heterocyclic group of the formula (i), (ii), (iii), or (iv):

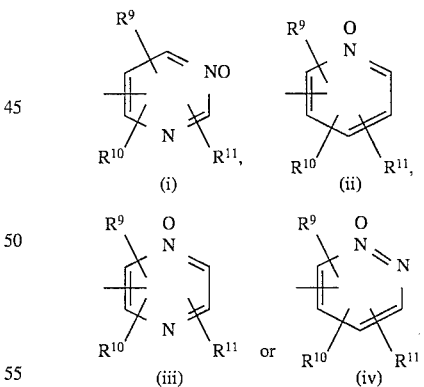

wherein $R^9$, $R^{10}$, and $R^{11}$ can be, amongst other groups, H.

European Patent Application, Publication No. 0 371 805, published Jun. 6, 1990, priority based on Japanese 303461/88 (30 Nov. 1988) and JP64059/89 (16 Mar. 1989) discloses compounds useful as hypotensives having the formula:

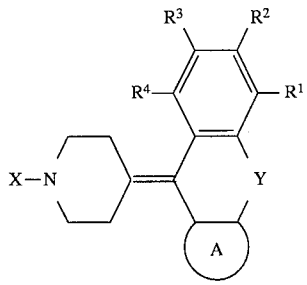

wherein: X represents an aralkyl- or aryl-containing group having from 6 to 30 carbon atoms; Y represents a heteroatom or an optionally substituted alkylene chain, the alkylene chain optionally containing hetero atom(s) or unsaturated bond(s); and A represents an optionally substituted condensed aromatic or heterocyclic ring. It is also disclosed that if present, the aromatic ring of X or A is benzene, pyridine, pyridazine, or pyrazine, amongst others. Amongst the specific compounds disclosed there is included: (1) 4-(5H-Dibenzo[a,d]cyclohepten-5-ylidene)-1-(2-Picolyl)piperidine; (2) 4-(5H-Dibenzo[a,d]cyclohepten-5-ylidene)-1-(3-Picolyl)piperidine; and (3) 4-(5H-Dibenzo[a,d]cyclohepten-5-ylidene)-1-(4-Picolyl)piperidine. It is believed the structures of these compounds are:

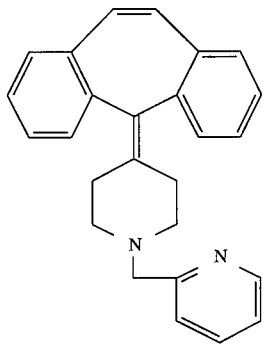
(1)

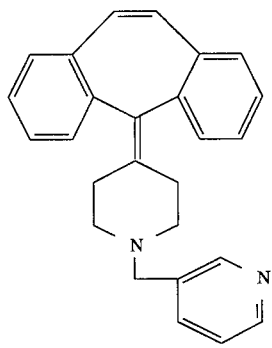
(2)

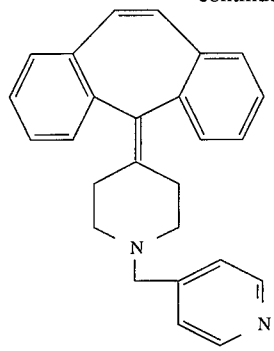
(3)

Galantay et al., Journal of Medicinal Chemistry, 1974, Vol. 17, No. 12, pp. 1316 to 1327 discloses oxazole and thiazole analogs of amitriptyline. A disclosed intermediate has the formula:

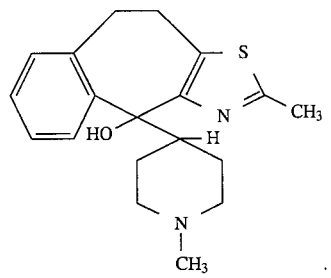

U.S. Pat. No. 4,659,716 discloses an intermediate of the formula:

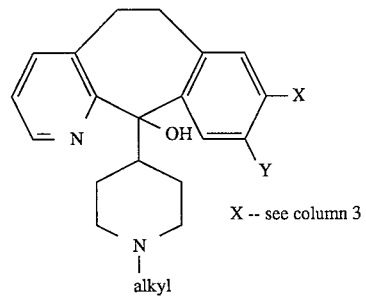

X — see column 3

PCT/US89/01689, International Publication Number WO 89/10363, published Nov. 2, 1989, which generically discloses compounds of this invention, discloses compounds of the formula:

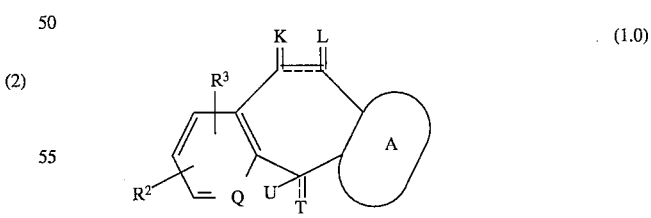
(1.0)

wherein T represents =O or

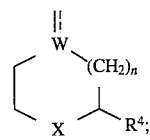

Q represents CH, N or N→O; ring A represents defined heterocyclic aromatic rings (see pp. 3 and 4 for example); U is —H or —OH when the bond between W and the cyclohepta ring is a single bond (see, for example, Compound 17 in Reaction f on page 17); W represents C, N or N→O and the dotted line drawn to W from the cyclohepta ring represents an optional double bond when W is C, or is absent when W is N→O; and X can be, amongst others:

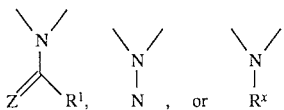

wherein Z is O or S; $R^1$ can be, amongst others, H, alkyl, cycloalkyl, aryl, and heteroaryl (the definition of heteroatom includes N→O); and $R^x$ can be alkyl, aralkyl or aryl.

SUMMARY OF THE INVENTION

We have now unexpectedly found that compounds having a —OH group attached to the carbon atom, of the tricyclic ring system, to which the piperidine ring is attached, and having a pyridine N-oxide group bound to the piperidine nitrogen through a C=Z group, provide surprisingly good activity as PAF antagonists. It is believed that many of these compounds, along with their reduced pyridine counterparts (i.e., L represents N), are also good antihistamines.

In particular, we have discovered such characteristics in compounds represented by Formula I:

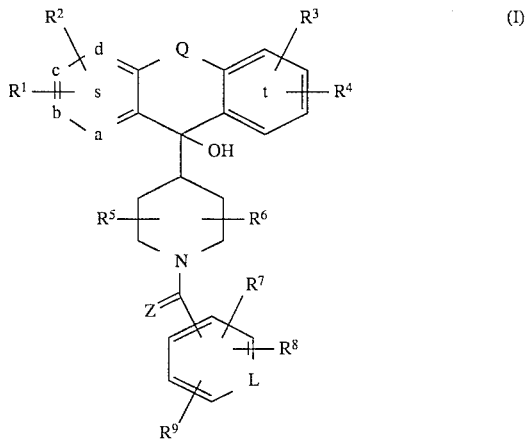

or a pharmaceutically acceptable salt or solvate thereof, wherein one of a, b, c, and d represents N or NO and the remaining others (i.e., the remaining a, b, c, and d) are C (carbon atoms); or all of a, b, c, and d represent carbon atoms;

L represents N or $N^+O^-$;

$R^1$, $R^2$, $R^3$, and $R^4$ are each independently selected from the group consisting of: H, halo, —$CF_3$, —$OR^{11}$, —C(O)$R^{11}$, —$SR^{11}$, —S(O)$_e R^{12}$ wherein e is 1 or 2, —N($R^{11}$)$_2$, —$NO_2$, —OC(O)$R^{11}$, —$CO_2 R^{11}$, —$OCO_2 R^{12}$, —CON($R^{11}$)$_2$, —$NR^{11}$C(=O)$R^{11}$, —CN, alkyl, aryl, alkenyl and alkynyl, said alkyl group is optionally substituted with —$OR^{11}$, —$SR^{11}$, —N($R^{11}$)$_2$ or —$CO_2 R^{11}$, and said alkenyl group is optionally substituted with halo, —$OR^{12}$ or —$CO_2 R^{11}$;

adjacent $R^1$ and $R^2$ groups can optionally be taken together to form a benzene ring fused to the ring s;

adjacent $R^3$ and $R^4$ groups can optionally be taken together to form a benzene ring fused to the ring t;

$R^5$ and $R^6$ are each independently selected from the group consisting of: H, alkyl and aryl; or $R^5$ can be taken together with $R^6$ to represent =O or =S;

$R^7$, $R^8$ and $R^9$ are each independently selected from the group consisting of: H, halo, —$CF_3$, —$OR^{11}$, —C(O)$R^{11}$, —$SR^{11}$, —S(O)$_e R^{12}$ wherein e is 1 or 2, —N($R^{11}$)$_2$, —$NO_2$, —CN, —$CO_2 R^{11}$, —$OCO_2 R^{12}$, —OC(O)$R^{11}$, —CON($R^{11}$)$_2$, —$NR^{11}$C(O)$R^{11}$, alkyl, aryl, alkenyl and alkynyl, said alkyl group is optionally substituted with —$OR^{11}$, —$SR^{11}$, —N($R^{11}$)$_2$, or —$CO_2 R^{11}$, and said alkenyl group is optionally substituted with halo, —$OR^{12}$ or —$CO_2 R^{11}$;

Q is selected from the group consisting of:

—O—, —S—, —$CH_2O$—, —$OCH_2$—, —$CH_2S$—,

—$SCH_2$—, —$NR^{10}$, —$CH_2NR^{10}$, —$NR^{10}CH_2$— and

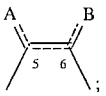

wherein the dotted line between carbon atoms 5 and 6 represents an optional double bond, such that when a double bond is present, A and B are each independently selected from the group consisting of: -$R^{11}$, —$OR^{12}$, halo and —OC(O)$R^{11}$, and when no double bond is present, A and B are each independently selected from the group consisting of: $H_2$, —(O$R^{12}$)$_2$, (alkyl and H), (alkyl)$_2$, (—H and —OC(O)$R^{11}$), (H and —$OR^{11}$), =O and =$NOR^{10}$;

$R^{10}$ is selected from the group consisting of: H and alkyl;

$R^{11}$ is selected from the group consisting of: H, alkyl and aryl;

$R^{12}$ is selected from the group consisting of: alkyl and aryl; and

Z is selected from the group consisting of: O and S, or Z optionally represents H and $R^{10}$.

In preferred compounds of Formula I, $R^1$, $R^2$, $R^3$, and $R^4$ are each independently selected from the group consisting of: H, halo, —$OR^{11}$, and alkyl, with H being most preferred; $R^5$ and $R^6$ are each independently selected from the group consisting of: H and alkyl, with H being most preferred; $R^7$, $R^8$, and $R^9$ are each independently selected from the group consisting of: H, halo, —$OR^{11}$, and alkyl, with H being most preferred; Q is selected from the group consisting of: —O—, —S—, —$NR^{10}$ (wherein $R^{10}$ is most preferably H or methyl),

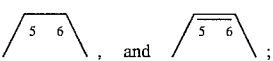

Z is selected from the group consisting of O, and H and $R^{10}$ wherein $R^{10}$ is preferably H; and L is $N^+O^-$.

Even more preferred compounds of this invention are represented by Formula IA:

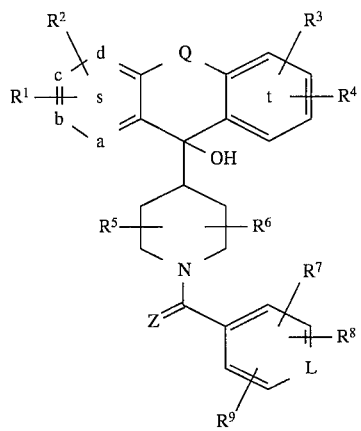
(IA)

wherein the substituents are as defined above for Formula I.

Still more preferred compounds are those of Formula IA wherein: $R^1$, $R^2$, $R^3$, and $R^4$ are each independently selected from the group consisting of: H, halo, —$OR^{11}$, and alkyl, with H being most preferred; $R^5$ and $R^6$ are each independently selected from the group consisting of: H and alkyl, with H being most preferred; $R^7$, $R^8$, and $R^9$ are each independently selected from the group consisting of: H, halo, —$OR^{11}$, and alkyl, with H being most preferred; Q is selected from the group consisting of:

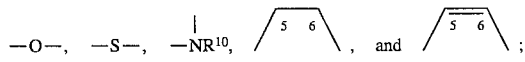

Z is selected from the group consisting of O, and H and $R^{10}$ wherein $R^{10}$ is preferably H; and L is $N^+O^-$.

Even more preferred compounds are those compounds of Formula IA wherein Q is selected from the group consisting of: —O—, —S—,

(wherein $R^{10}$ is most preferrably methyl), and

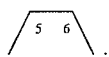

Representative compounds of this invention include, but are not limited to:

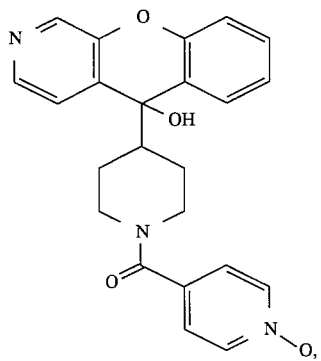
(IA-1)

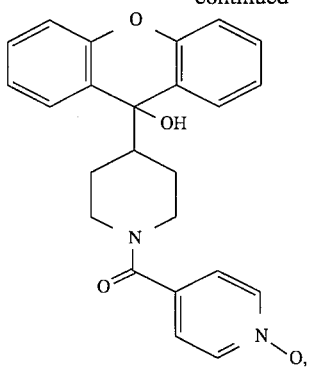
(IA-2)

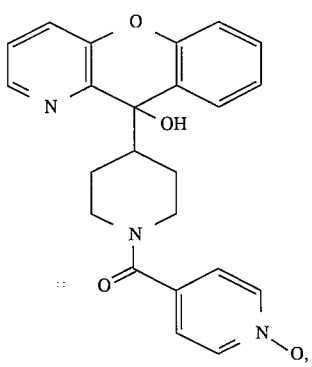
(IA-3)

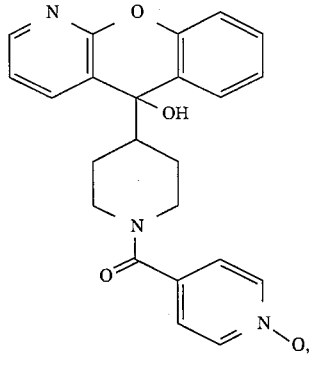
(IA-4)

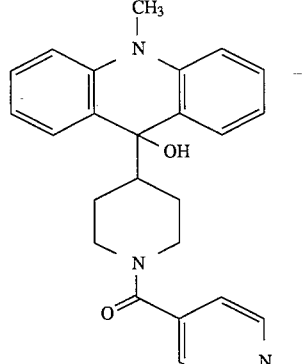
(IA-5)

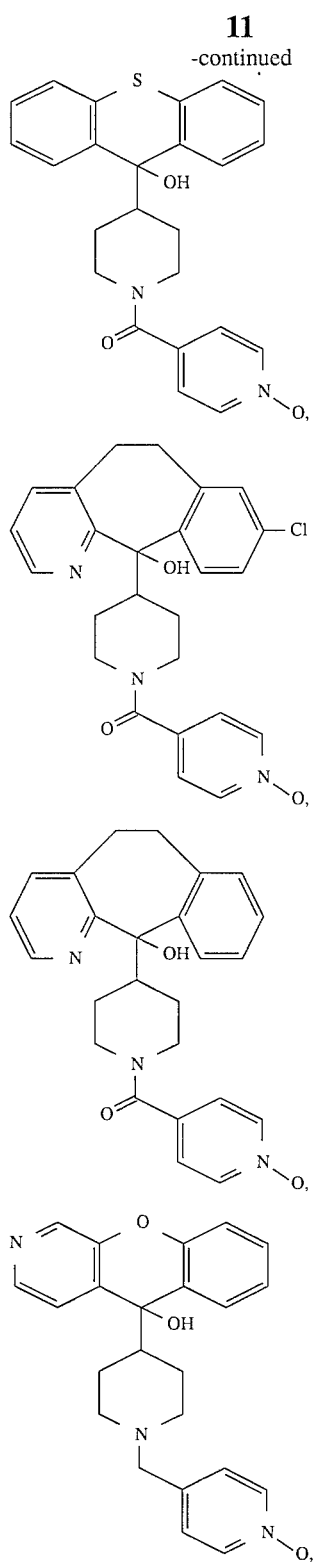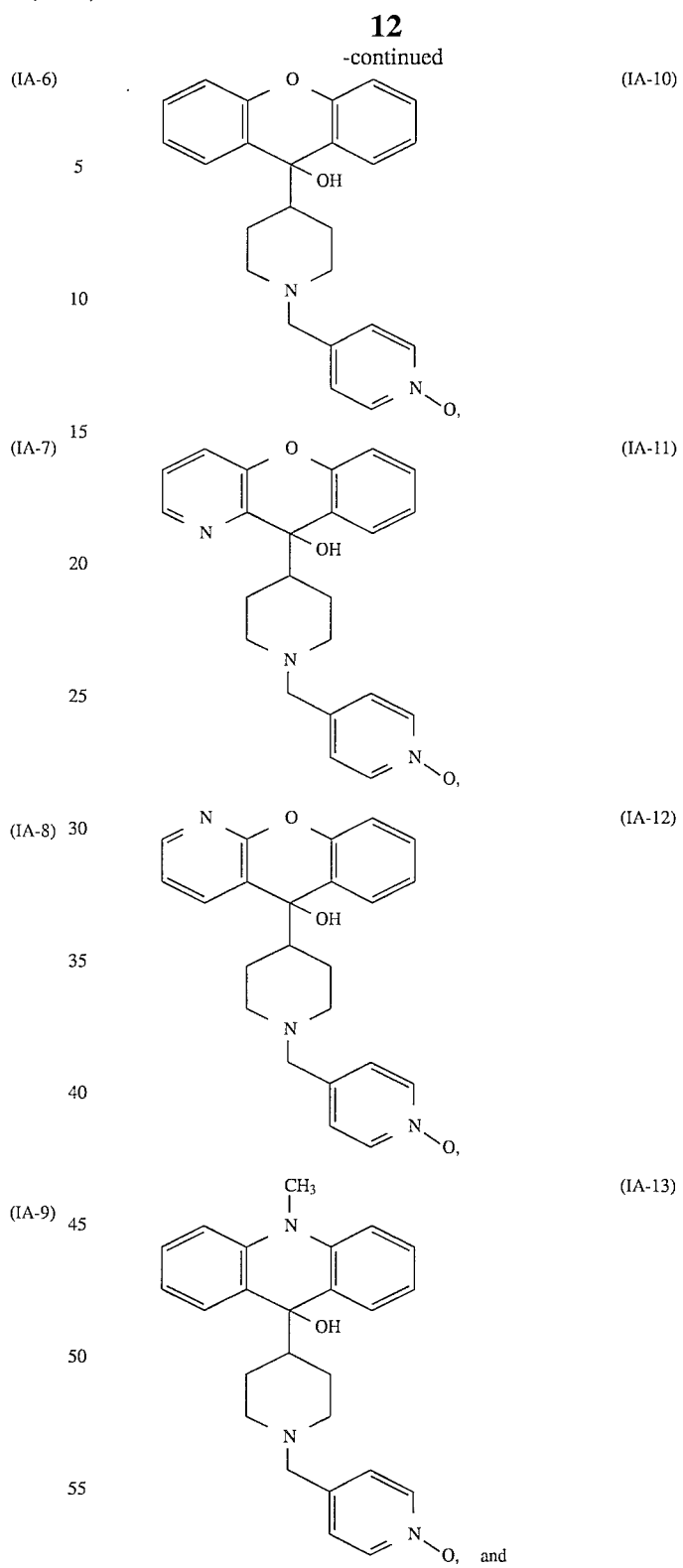

13

-continued

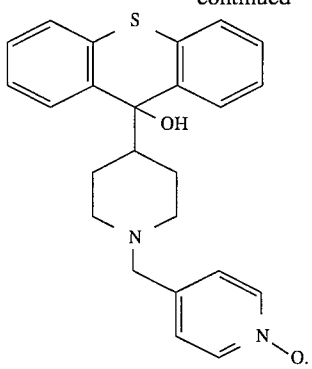

(IA-14)

This invention also provides a pharmaceutical composition comprising an effective amount of a compound of Formula I in combination with a pharmaceutically acceptable carrier.

This invention further provides a method for treating allergic reaction in a mammal comprising administering to the mammal an effective anti-allergic amount of a compound of Formula I.

Additionally, this invention provides a method for treating inflammation in a mammal comprising administering to the mammal an effective anti-inflammatory amount of a compound of Formula I.

DETAILED DESCRIPTION OF THE INVENTION

As used herein, the following terms are used as defined below unless otherwise indicated:

alkyl—(including the alkyl portions of alkoxy, alkylamino and dialkylamino)—represents straight and branched carbon chains and contains from one to twenty carbon atoms, preferably one to six carbon atoms;

alkenyl—represents straight and branched carbon chains having at least one carbon to carbon double bond and containing from 2 to 12 carbon atoms, preferably from 2 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_e$R$^{12}$ (wherein e is 1 or 2 and R$^{12}$ is alkyl or aryl), —CF$_3$, amino, alkylamino, dialkylamino, —COOR$^{12}$ or —NO$_2$; and halo—represents fluoro, chloro, bromo and iodo.

Also, unless indicated otherwise, the following abbreviations used herein have the following meanings:

CDI—N,N'-carbonyldiimidazole;

DCC—N,N'-dicyclohexylcarbodiimide;

DEC—1-(3-dimethylaminopropyl)-3-ethylcarbodiimide hydrochloride;

eq—equivalents;

HOBT—1-hydroxybenzotriazole hydrate; and

THF—tetrahydrofuran.

14

Certain compounds of the invention may exist in different isomeric (e.g., enantiomers and diastereoisomers) as well as conformational forms. The invention contemplates all such isomers both in pure form and in admixture, including racemic mixtures. Enol forms are also included. For example, hydroxy substituted pyridinyl groups can also exists in their keto form:

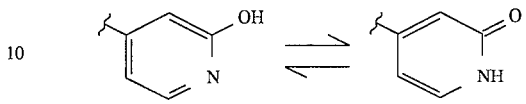

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

As noted above, the pyridine and benzene ring structures of Formula I may contain one or more substituents R$^1$, R$^2$, R$^3$ and R$^4$, and the pyridine ring containing L may contain one or more substituents R$^7$, R$^8$, and R$^9$. In compounds where there is more than one substituent on a ring, the substituents may be the same or different. Thus compounds having combinations of such substituents are within the scope of the invention. Also, the lines drawn into the rings from the R$^1$, R$^2$, R$^3$, R$^4$, R$^7$, R$^8$, and R$^9$ groups indicate that such groups may be attached at any of the available positions. For example, the R$^1$ and R$^2$ groups may be attached to a carbon atom at any of the a, b, c or d positions.

R$^5$ and R$^6$ are attached to the piperidyl ring. As such they may be the same or different. The variables R$^5$ and R$^6$ in addition to representing H, may represent variables attached to the same or different carbon atoms in said ring. For example, when R$^5$ and R$^6$ are combined to represent =O or =S, they are attached to the same carbon atom.

The N-oxides are illustrated herein using the terms NO, N→O, N—O and N$^+$O$^-$. All are considered equivalent as used herein.

Lines drawn into the ring systems indicate that the indicated bond may be attached to any of the substitutable ring carbon atoms.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention. All such acid and base salts are intended to be pharmaceutically acceptable salts within the scope of the invention and all acid and base salts are considered equivalent to the free forms of the corresponding compounds for purposes of the invention.

The following processes can be employed to produce compounds of Formula I (i.e., IA–IF). Those skilled in the art will recognize that the reactions are conducted under conditions, e.g., temperature, that will allow the reaction to proceed at a reasonable rate to completion. Also, unless indicated otherwise, the substituents for the formulas given hereinafter have the same definition as those of Formula I.

Process A—Compounds of Formula I wherein Z is O (oxygen) (i.e., IB)

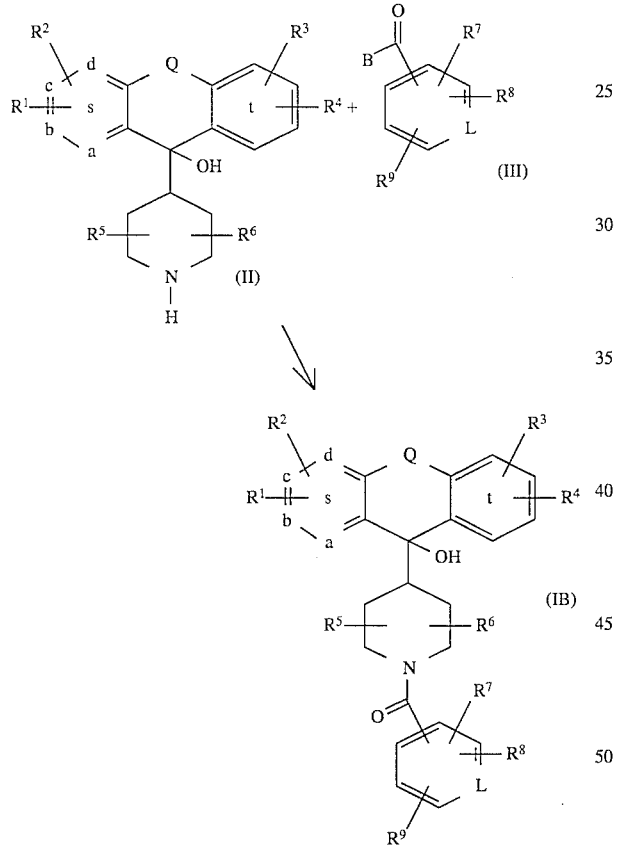

A compound of Formula II can be reacted with a compound of Formula III to produce a compound of Formula IB wherein Z is O. In the preferred method, B is hydroxy and a coupling reagent is employed to produce compounds of Formula IB. The reaction can be conducted in an inert solvent, such as THF or methylene chloride (with methylene chloride usually being preferred), at a temperature of about $-15°$ C. to reflux. Examples of coupling agents include DCC, DEC, and CDI.

If B represents a suitable leaving group other than hydroxy, for example a halide (such as Cl, Br, or I) or —O(CO)$R^{12}$, then a suitable base is usually present. The reaction is usually conducted in an inert solvent, such as tetrahydrofuran (THF) or methylene chloride, and at a suitable temperature, such as a temperature of about $-15°$ C. to reflux. Suitable bases include pyridine and triethylamine. The use of a base can often be omitted when the compound of Formula II contains a basic amine functionality (e.g., one of a, b, c, or d is nitrogen).

When B is alkoxy (—$OR^{12}$), compounds of Formula IB may be produced by refluxing a compound of Formula II with an excess of a compound of Formula III in an inert solvent such as THF, methylene chloride or toluene.

Process B—Compounds of Formula I wherein Z is H and $R^{10}$ (i.e., IC)

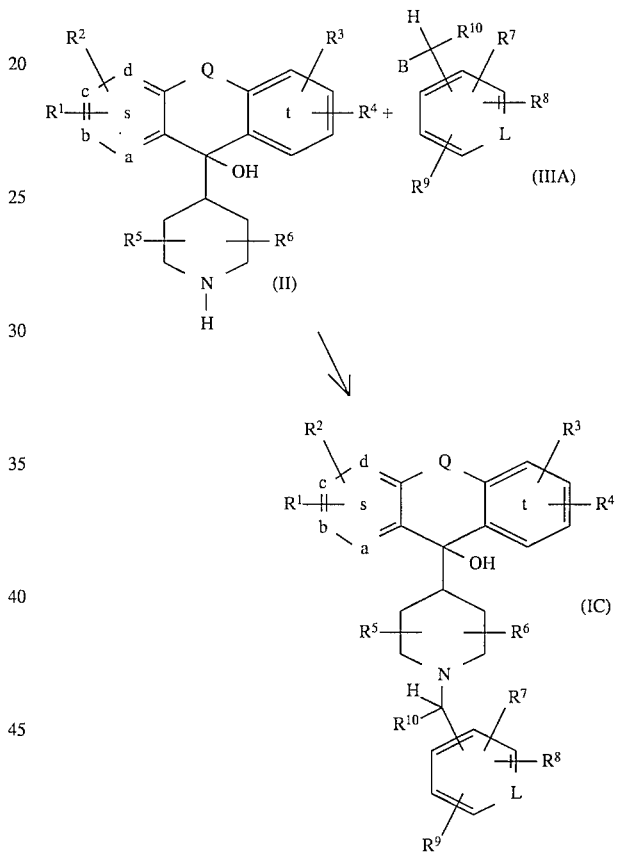

In the preferred method, a compound of Formula II can be reacted with a compound of Formula IIIA in the presence of a base to produce compounds of Formula IC wherein Z is H and $R^{10}$. The reaction is usually conducted in an inert solvent such as THF or methylene chloride at a suitable temperature, usually at reflux, although lower temperatures can be employed, for example about 0° C. to reflux. Suitable bases include pyridine and triethylamine. The use of a base can be omitted when the compound of Formula II contains a basic amine functionality (e.g., either a, b, c, or d is nitrogen). B designates a suitable leaving group such as halo, (e.g., Br or Cl), mesyl, tosyl or the like.

Alternatively, the compounds of Formula IC may be prepared via reductive amination of the compound of Formula II with the pyridincarboxaldehyde of Formula IV:

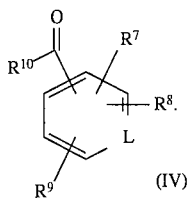

(IV)

The reaction can be carried out in a polar solvent, such as an alcohol (e.g., methanol or ethanol) with the optional use of a water scavenger, such as a 3 Å molecular sieve. The intermediate Schiff Base which is formed is reduced with $H_2$ in the presence of a Pd/C catalyst or a reducing agent, such as sodium cyanoborohydride ($NaCNBH_3$). The reaction takes place at a temperature of about 0° to about 100° C. based on the solvent used.

Compounds of Formula IC, wherein $R^{10}$ is H, may be prepared via reduction of the corresponding amides of Formula IB. Treatment of Formula IB with lithium aluminum hydride ($LiAlH_4$), or similar known reducing agents, reduces the carbonyl of Formula IB, thus, providing compounds of Formula IC wherein $R^{10}$ is H. The reaction is typically carried out in an inert solvent at a temperature of about 0° C. to reflux. Usually an etheral solvent such as THF or diethyl ether is used. This method is limited to cases where the reducing agent will not effect the reduction of other functional group such as esters and ketones.

Process C—Compounds of Formula I wherein Z is O and L is N (i.e., ID)

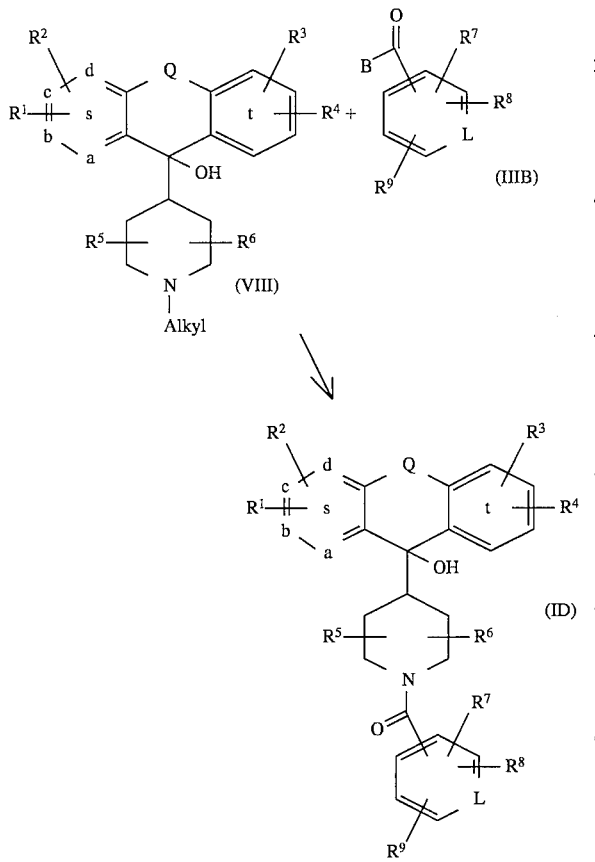

Compounds of Formula ID wherein, L is N, may be prepared directly by reacting a compound of Formula VIII with a compound of Formula IIIB. Preferably, the reaction can be run in the presence of a suitable nucleophile (e.g., LiI and the like) in an inert solvent, such as toluene, dioxane or xylenes. B in Formula IIIB is a suitable leaving group, such as halo (e.g., Br or Cl) or $-OC(O)R^{12}$. A suitable base (such as $K_2CO_3$ or $Cs_2CO_3$) can be added and heating is usually required. Typically, a temperature of about 50° to about 300° C. (preferably about 100° to about 175° C.) can be utilized depending on the boiling point of the solvent.

Process D—Compounds of Formula I wherein Z is S and L is N (i.e., IE)

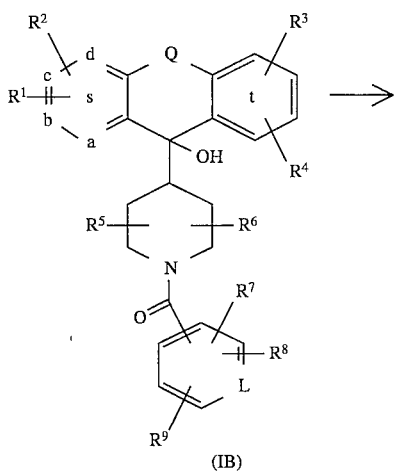

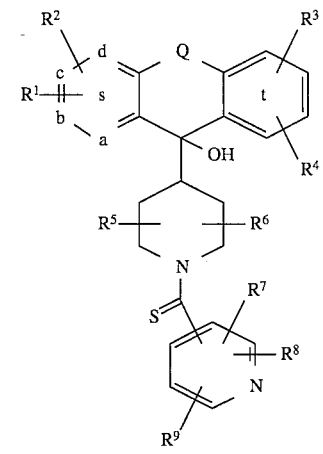

Compounds of Formula IE can be prepared by reacting a compound of Formula IB with $P_2S_5$, Lawesson's reagent or other suitable reagent known in the art for introducing sulfur in place of oxygen. The reaction can usually be conducted at an elevated temperature, such as about 80° to about 150° C. in a solvent such as pyridine, toluene (preferred) or xylene.

Process E—Compounds of Formula I wherein Z is O (oxygen) and L is NO (i.e., IF)

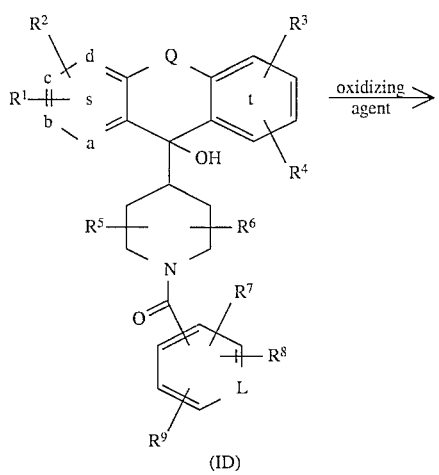

(ID)

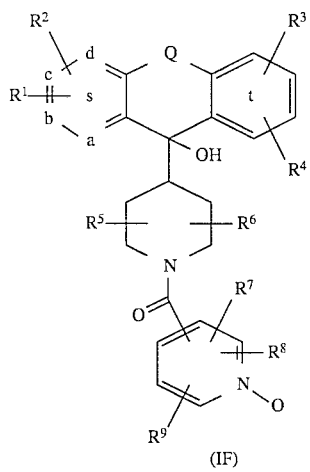

(IF)

This may be accomplished with a suitable oxidizing agent in an inert solvent such as meta-chloroperbenzoic acid (MCPBA) in methylene chloride or hydrogen peroxide in acetic acid. The reaction is usually conducted at a temperature of about −15° C. to reflux. When present, oxidation of other basic amino groups in the molecule (e.g., —$NH_2$, —$N(CH_3)_2$ and the like) can occur with this method; however, in such cases, with excess reagent the N-oxides of Formula IF can be produced. Compounds of Formula ID wherein L is nitrogen (L=N) are prepared as described in methods described in processes A and C.

Preparation of Intermediate Compounds

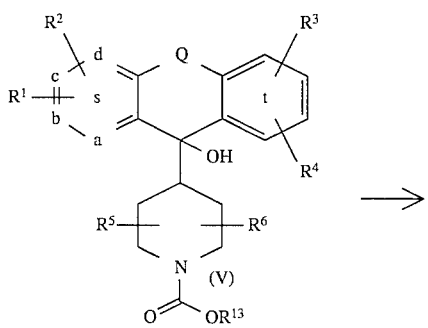

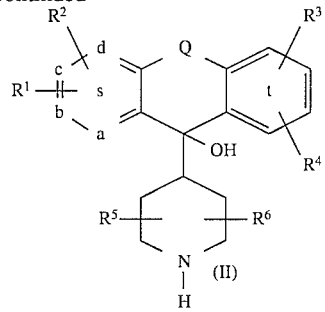

(II)

Compounds of Formula II can be prepared by removal of the carbamoyl moiety ($COOR^{13}$) wherein $R^{13}$ can be, for example alkyl, aryl or halogenated alkyl (e.g., trichloroethyl) from the corresponding carbamate of Formula V via either acid (e.g., HCl/$H_2O$/heat) or base (e.g., KOH/ethanol/$H_2O$/heat) hydrolysis. The reaction is usually carried out between about 80° C. to reflux depending on the solvent of choice.

Alternatively, depending upon the nature of $R^{13}$, as determined by one skilled in the art, the compound of Formula V can be treated with an organometallic reagent (e.g., $CH_3Li$ for $R^{13}$=$CH_3$), with a reductive reagent (e.g., Zn in acid for $R^{13}$=$CH_2CCl_3$), with an alcohol or water (e.g., for $R^{13}$= $CHClCH_3$), or with hydrogen and a noble metal catalyst such as palladium on carbon (e.g., Pd/C and $H_2$ for $R^{13}$= aralkyl such as benzyl, and the like) to form compounds of Formula II.

Compounds of Formula II can also be obtained from the corresponding nitrile of Formula VI:

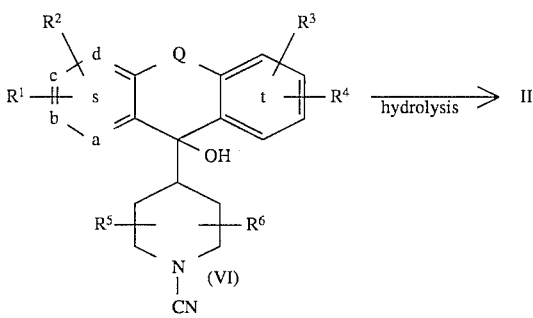

via either acid hydrolysis (e.g., HCl/$H_2O$/heat (about 90° to about 100° C.)) or base hydrolysis (e.g. KOH/ethanol/$H_2O$/heat (about 90° to about 100° C.)). The reaction can be conducted at reflux.

Compounds of Formula II can also be prepared from compounds of Formula VIIA wherein Q is O or S, and $R^{14}$ represents alkoxylcabonyl (for example, —C(O)$OR^{15}$ wherein $R^{15}$ represents an alkyl group having 1 to 6 carbons). Compounds of Formula II can also be prepared from compounds of Formula VIIB wherein Q is O or S, and $R^{14}$ represents —C(O)H. Both reactions can be carried out by treating compounds of Formulas VIIA or VIIB with concentrated HCl and water under reflux.

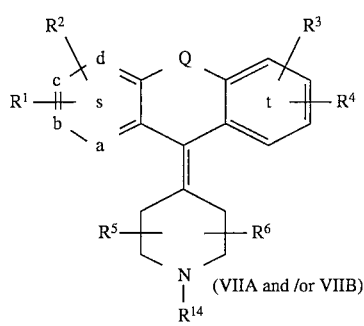

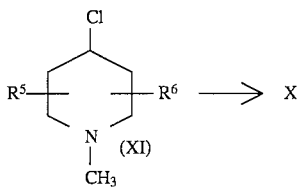

Compounds of Formula X can be prepared from the 1-methyl-4-chloro-piperidine of Formula XI:

by reaction with the appropriate alkyl or aryl chloroformate in an inert solvent (e.g., toluene) at a temperature of about 50° to about 120° C. This procedure is disclosed in U.S. Pat. No. 4,282,233, U.S. Pat. No. 4,355,036 and WO 88/03138, the disclosures of which having already been incorporated herein by reference thereto.

Compounds of Formula V can be prepared from the N-alkyl (preferably N-methyl) compounds of Formula VIII:

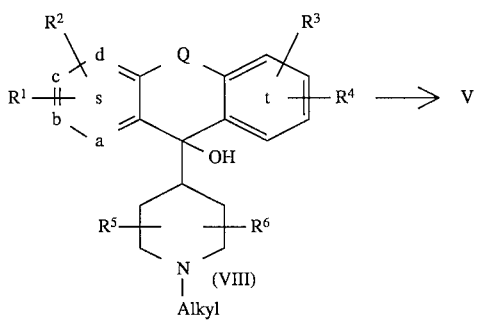

Compounds of Formula VI can be prepared from compounds of Formula VIII by the well known von Braun reaction (for example, J. V. Braun, Ber. 44, 1250 (1911)). For example, treatment of a compound of Formula VIII with cyanogen bromide (BrCN) in an inert solvent (e.g., toluene or benzene) at a temperature of about 50° to about 120° C. would provide the nitrile of Formula VI.

Compounds of Formula VIIA wherein Q is O or S and $R^{14}$ represents alkoxycarbonyl (e.g., $-CO_2$ $C_2H_5$ or $CO_2CH_2CCl_3$) can be prepared from compounds of Formula XII:

by reacting the compound of Formula VIII with a suitable alkyl, aryl or halogenated alkyl (e.g., trichloroethyl) chloroformate to provide the desired carbamate (e.g., ethylchloroformate, using a temperature of about 50° C. to reflux, usually about 50° to about 90° C., in an inert solvent, such as toluene or benzene). The procedure is disclosed in U.S. Pat. No. 4,282,233, U.S. Pat. No. 4,355,036 and WO 88/03138, the disclosures of which are incorporated herein by reference thereto.

Compounds of Formula V can also be prepared by

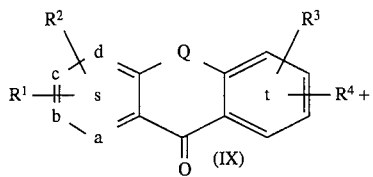

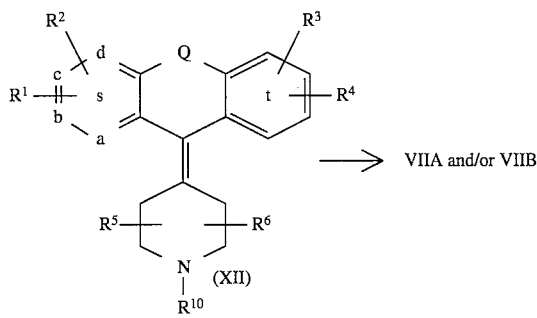

wherein $R^{10}$ is an alkyl group, preferably methyl, using the method disclosed above for the preparation of compounds of Formula V from the compounds of Formula VIII.

Compounds of Formula VIIB wherein Q is O or S, and $R^{14}$ represents a formyl (—CHO) group, can be prepared by treating compounds of Formula XII, wherein $R^{10}$ is H, with ethylformate as a solvent under reflux. Preferably, the reaction is continued overnight.

The compound of Formula XII

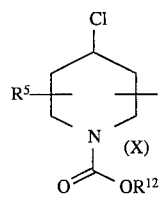

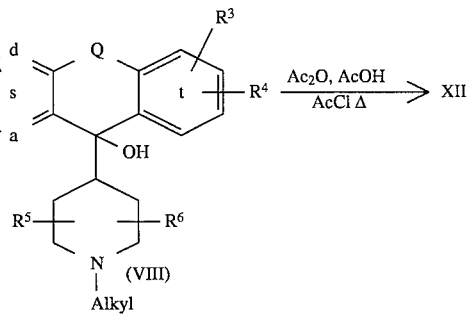

alkylation of the ketone of Formula IX with a compound of Formula X wherein $R^{12}$ represents an alkyl group containing 1 to 6 carbon atoms with ethyl being preferred, or aryl. The reaction can be conducted in an inert solvent such as THF or diethyl ether with liquid ammonia as a co-solvent in the presence of 2 equivalents of sodium metal.

can be prepared by refluxing the compound of Formula VIII in acetic acid in the presence of acetic anhydride and acetyl chloride for a period of 10 to 24 hours.

Compounds of Formula VIII can be prepared by treating the ketone of Formula IX with a Grignard reagent of Formula XIII:

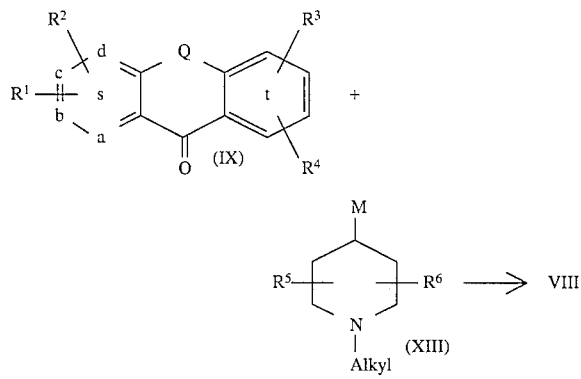

(wherein M is MgCl or Na) in an inert solvent, such as diethyl ether, benzene, or THF. Preferably, the N-alkyl group is a methyl group. The reaction can be conducted at a temperature of about 0° C. to about room temperature in an argon atmosphere. The reaction mixture can be quenched with $NH_4Cl$ to form the compound of Formula VIII. If sodium metal is used, liquid ammonia is used as a co-solvent.

The compound of Formula XIII can be prepared by procedures known in the art from magnesium and the 4-chloro N-substituted (preferably N-methyl) piperidine.

Those skilled in the art will appreciate that many of the substituents ($R^1$–$R^9$, A, and B) present in the various intermediates of the synthetic sequences described above can be used to generate different substituents by methods known to those skilled in the art. For example, a ketone can be converted to a thioketone via its treatment with $P_2S_5$ or Lawesson's reagent. These reagents introduce sulfur in place of oxygen. The reaction may take place at room or higher temperatures in pyridine, toluene or other suitable solvents. A ketone can also be converted to an alkyl or aryl group. This is accomplished via treatment of the ketone with a Wittig reagent or other organometalic species (e.g., Grignard reagent) to produce the corresponding olefin or alcohol, respectively. These derivatives in turn can be converted to the alkyl or aryl compounds.

In the above processes, in accordance with procedures well known to those skilled in the art, it is sometimes desirable and/or necessary to protect certain groups during the reactions. Certain protecting groups are employed in the above processes but, as those skilled in the art will recognize, other protecting groups may be used in their place. Conventional protecting groups are operable as described in Greene, T. W., "Protective Groups In Organic Synthesis," John Wiley & Sons, New York, 1981; the disclosure of which is incorporated herein by reference thereto. After the reaction or reactions, the protecting groups can be removed by standard procedures.

The compounds of the invention possess platelet-activating factor ("PAF") antagonistic properties and are believed to have histamine antagonistic properties. The compounds of the invention are, therefore, useful when PAF and/or histamine are factors in the disease or disorder. This includes allergic diseases such as asthma, allergic rhinitis, adult respiratory distress syndrome, urticaria and inflammatory diseases such as rheumatoid arthritis and osteo-arthritis. For example, PAF is an important mediator of such processes as platelet aggregation, smooth muscle contraction (especially in lung tissue), eosinophil chemotxis, vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. In Vitro Studies—Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 ml) was collected from healthy male donors in an anticoagulant solution (5 ml) containing sodium citrate (3.8%) and dextrose (2%). Blood was centriguged at 110×g for 15 min. and the supernatant platelet-rich plasma (PRP) carefully transferred into a polypropylene tube. Platelet-poor-plasma (PPP) was prepared by centrifuging PRP at 12,000×g for 2 min. (Beckman Microfuge B). PRP was used within 3 hr. of drawing the blood.

PAF was dissolved in chloroform:methanol (1:1, v/v) at a concentration of 2 mg/ml and stored at −70° C. An aliquot of this solution was transferred to a polypropylene tube and dried under a flow of nitrogen gas. To the dried sample was added Hepes-saline-BSA (BSA=bovine serum albumen) buffer (25 mM Hepes, pH 7.4, 1254 mM NaCl, 0.7 mM $MgCl_2$ and 0.1% BSA) to obtain a 1 mM solution and sonicated for 5 min. in a bath sonicator. This stock solution was further diluted to appropriate concentrations in Hepes-saline-BSA buffer. Collagen (Sigma) and adenosine diphosphate (ADP) (Sigma) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer (Model 440, Chrono-Log Corp., Havertown, Pa.). PRP (0.45 ml) in aggregometer cuvettes was continually stirred (37° C.). Solutions (50 μL) of test compounds or vehicel were added to the PRP and, after incubation for 2 min., 10–15 μl aliquots of PAF solution were added to achieve a final concentration of $1-5×10^{-8}M$. In different experiments the aggreatory response was kept within a set limit by varying the concentration of PAF. Incubations were continued until the increase in light transmission reached a maximum (usually 2 min.). This increase in light transmission reflecting platlet aggregation is transmitted to a computer by the Chrono-Log model 810 AGGRO/LINK interface. The AGGRO/LINK calculates the slope of transmission change, thus providing the rate of aggregation. Values for inhibition were calculated by comparing rates of aggregation obtained in the absence and the presence of the compound. For each experiment, a standard PAF antagonist such as 8-chloro-6,11-dihydro-11-(1-acetyl-4 -piperidylidene)-5 H-benzo[5,6]cyclohepta[1,2-b]pyridine was used as a positive control.

Compounds that inhibit PAF-induced aggregation were tested against several other aggregating agents including collagen (0.2 mg/ml) and ADP (2 μM). Compounds showing no activity against these latter agents were considered to be specific PAF antagonists. Results are shown in TABLE 1 below.

B. In Vivo Studies: Agonist-Induced Responses—Spasmogen-Induced Bronchospasm in Guinea Pigs Male Hartley guinea pigs (450–550 g) were obtained from Charles River Breeding Laboratories. The animals were fasted overnight and the following day were anesthetized with 0.9 ml/kg i.p. of dialurethane (containing 0.1 g/ml diallylbarbituric acid, 0.4 g/ml ethylurea and 0.4 g/ml urethane). The left jugular vein was cannulated for the administration of compounds. The trachea was cannulated and the animals were ventilated by a rodent respirator at 55 strokes/min. with a stroke volume of 4 ml. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg), methacholine (10 μg/kg), 5-hydroxytryptamine (10 μg/kg), or PAF (0.4 μg/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in TABLE 1 below.

TABLE 1

| CMPD NO | PAF Antagonism (in vitro) $IC_{50}$ (μM) | Agonist Bronchospasm (in Vivo)-oral | | | |
|---|---|---|---|---|---|
| | | PAF | | Histamine | |
| | | Dose | % Inhibition | Dose | % Inhibition |
| IA-1 | 5.0 | — | — | — | — |
| IA-2 | 5.0 | — | — | — | — |
| IA-3 | 2.0 | 3 mpk | 97 | 3 mpk | 0 |
| IA-4 | 0.8 | — | — | — | — |
| IA-5 | 5.0 | 3 mpk | 7 | — | — |
| IA-6 | 1.5 | 3 mpk | 20 | — | — |
| IA-8 | 2 | 3 mpk | 25 | — | — |
| IA-9 | >10 | — | — | — | — |
| IA-10 | 10 | — | — | — | — |
| IA-11 | 5.0 | — | — | — | — |
| IA-12 | 3.0 | 3 mpk | 42 | 3 mpk | 0 |
| IA-14 | 1.75 | — | — | — | — |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application. The appropriate dosage can be determined by comparing the activity of the compound with the activity of a known PAF and histamine antagonist such as 8-chloro-6,11-dihydro-11-(1-acetyl-4-piperidylidene)-5H-benzo[5,6]cyclohepta[1,2-b]pyridine, which compound is disclosed in U.S. Pat. No. 4,826,853.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 1500 mg/day preferably 10 to 1000 mg/day, in two to four divided doses to achieve relief of the symptoms. The compounds are non-toxic when administered within this dosage range.

The invention disclosed herein is exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

A.

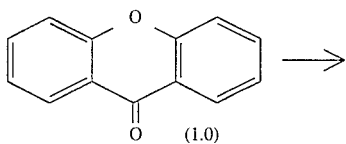

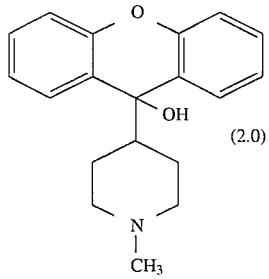

To a cool (ice/H₂O bath) solution of xanthone (4.0 g in THF (60 mL), Formula 1.0, was added a 1.2M solution of N-methyl 4-piperidyl magnesium chloride (20 mL). The reaction was allowed to stir for 1 hour while warming to room temperature. The reddish reaction mixture was then poured into ice water, followed by quenching with a saturated ammonium chloride solution. The white precipitated product was filtered to give 5.0 g (83% yield) of the compound of Formula 2.0.

B.

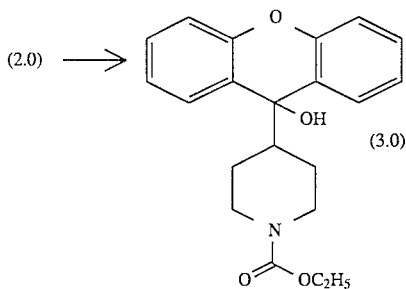

To a hot solution (in a 80°–90° C. oil bath) of compound 2.0 (2.2 g) and triethylamine (3.12 mL, 3.0 eq.) in toluene (35 mL) was added ethylchloroformate (3.57 mL, 50 eq.) dropwise in 20 minutes. The reaction was heated at this temperature for about 1.5 hours or until no starting material could be detected by TLC (developing solvent: 50% ethyl acetate in hexane). The reaction was then cooled and diluted with ethyl acetate. The resulting reaction mixture was then washed once with water, once with brine, and then dried (Na₂SO₄). The reaction mixture was then filtered and the solvent was removed under vacuum on a rotory evaporator. The crude product was purified by chromatography on silica gel (eluted with 25% ethyl acetate in hexanes), and then recrystallized from acetone and pentane to give the compound of Formula 3.0, 1.71 g (66% yield), m.p. 142°–144° C. as a white crystalline solid.

C.

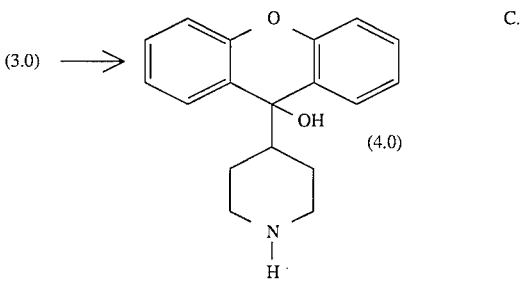

The compound of Formula 3.0 (0.55 g) was hydrolyzed in concentrated hydrochloric acid and water (70:30 by volume, 50 mL) by heating the solution in an oil bath (100° C.) for 8 hours followed by stirring at room temperature for overnight. The reaction mixture was poured into ice/water and then basified to pH 8–9 with a 25% NaOH solution. Then the reaction mixture was extracted with CH₂Cl₂, dried (Na₂SO₄) and filtered. The solvent was removed on a rotory evaporator under vacuum and the product was recrystallized from methanol and CH₂Cl₂ to give the compound of Formula 4.0, 0.223 g (51% yield), m.p. 237–238, as an off-white solid.

By utilizing the starting materials, Formulas 5.0, 7.0, and 9.0 listed in Table 2 below, and employing procedures similar to that described in Steps A to C of Preparative Example 1, then the compounds of Formulas 6.0, 8.0 and 10.0, respectively were prepared.

TABLE 2

| Starting Material | Product | m.p. |
|---|---|---|
| (5.0) | (6.0) | 112–114° C. |

TABLE 2-continued

| Starting Material | Product | m.p. |
|---|---|---|
| 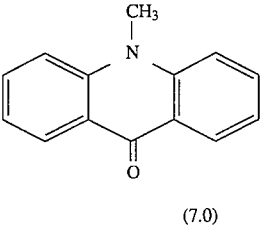 (7.0) | 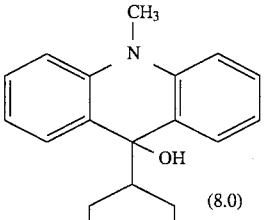 (8.0) | — |
| 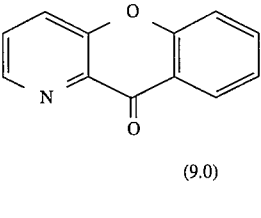 (9.0) | 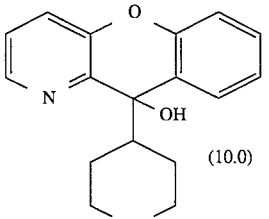 (10.0) | — |

PREPARATIVE EXAMPLE 2

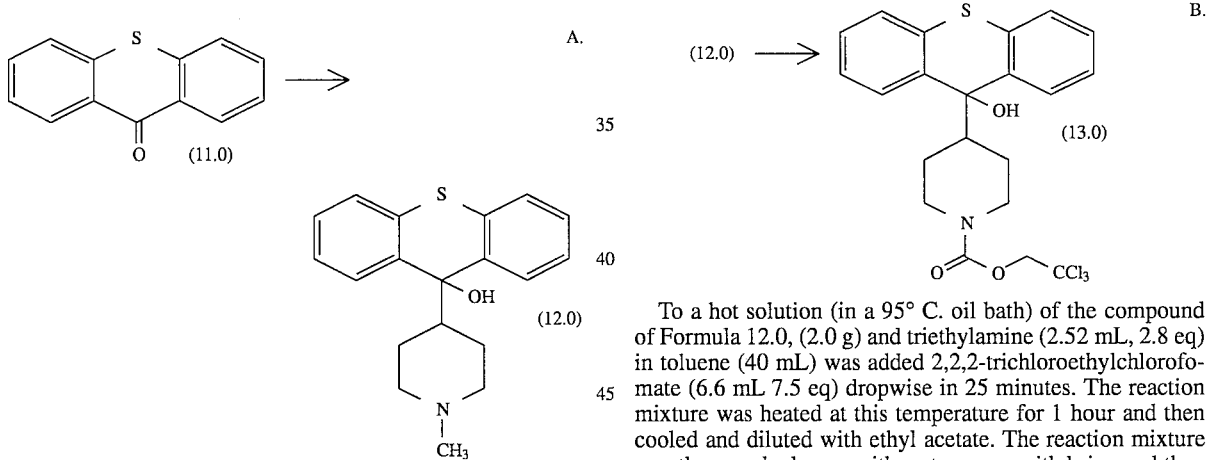

To a cool (ice/H$_2$O bath) solution of thioxanthen-9-one, Formula 11.0, (4.0 g) in THF (60 mL) was added a 1.2M solution of N-methyl-4-piperidyl magnesium chloride (40 mL). The ice bath was removed and the reaction mixture was stirred for 30 minutes at room temperature, and then the reaction was quenched with NH$_4$Cl solution. The reaction mixture was extracted with ethyl acetate and washed once with brine and then dried (Na$_2$ SO$_4$). The reaction mixture was then filtered and the solvent was removed under vacuum to give a crude product. The crude product was recrystallized from ethyl acetate and diisopropyl ether (80:20) to give the compound of Formula 12.0, 4.35 g, as a solid.

To a hot solution (in a 95° C. oil bath) of the compound of Formula 12.0, (2.0 g) and triethylamine (2.52 mL, 2.8 eq) in toluene (40 mL) was added 2,2,2-trichloroethylchloroformate (6.6 mL 7.5 eq) dropwise in 25 minutes. The reaction mixture was heated at this temperature for 1 hour and then cooled and diluted with ethyl acetate. The reaction mixture was then washed once with water, once with brine and then dried (Na$_2$SO$_4$). The reaction mixture was then filtered and the solvent was removed. The compound of Formula 13.0, 1.64 g, was obtained as a tan powder.

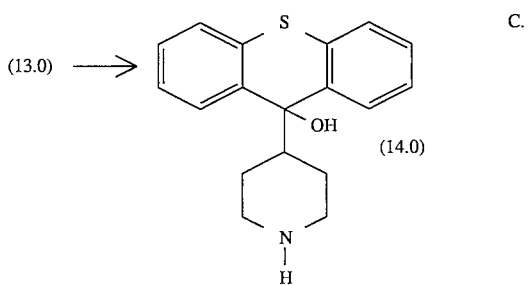

A mixture of the compound of Formula 13.0, (0.56 g), and zinc dust (1.5 g) in glacial acetic acid (22 mL) was heated in an oil bath (70° C.) for 2 hours. The reaction mixture was cooled and then filtered. The acetic acid was removed on a rotory evaporator with a mechanical pump and the residue was basified to pH=8 with a 6N NaOH solution. This mixture was then extracted with $CH_2Cl_2$, and the $CH_2Cl_2$ was then washed once with brine and then dried ($Na_2SO_4$). The mixture was then filtered and the solvent was removed on a rotory evaporator with vacuum to give the compound of Formula 14.0, 238 mg, as a solid.

The compound of Formula 15.0 used in the procedures similar to those described in steps A through C of Preparative Example 2, produced the compound of Formula 16.0:

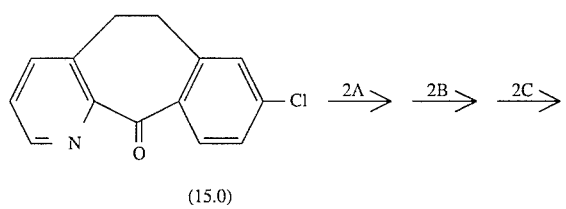

(15.0)

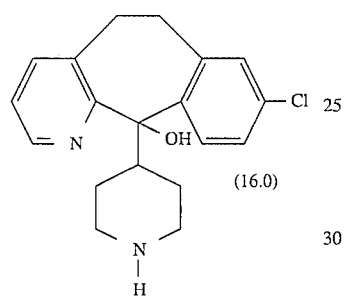

(16.0)

PREPARATIVE EXAMPLE 3

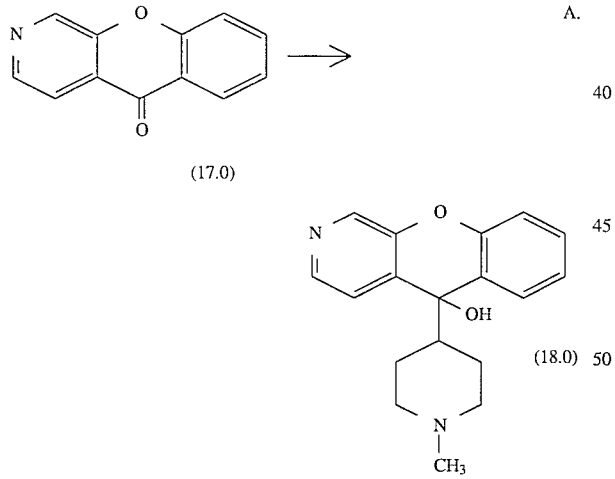

To a solution of sodium metal (3.0 g) in 500 mL anhydrous liquid ammonia was added a suspension of a compound of Formula 17.0 (11.8 g) in THF (250 mL). This mixture was stirred for 1 hour and then a solution of N-methyl-4-chloropiperidine (8.0 g) in THF (250 mL) was dripped in. The reaction mixture was stirred for 2.5 hours. Solid $NH_4Cl$ and water were slowly added sequentially to the reaction mixture. The mixture was extracted with $CHCl_3$. The extract ($CHCl_3$ layer) was washed with water and then dried ($Na_2SO_4$). The solvent was removed with vacuum on a rotory evaporator and the resulting product was recrystallized from $CH_3CN$ to give the compound of Formula 18.0, 12.3 g, m.p. 155°–157° C.

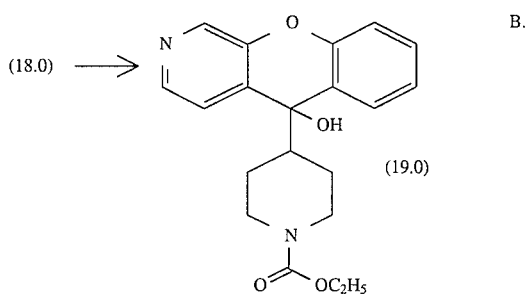

B.

To a hot solution (in a 90° C. oil bath) of the compound of Formula 18.0 (3.0 g) and triethylamine (3.82 mL) in dry toluene (50 mL) was added ethylchloroformate (9.56 mL) dropwise in 40 minutes. The reaction mixture was stirred continuously for 2 hours at this temperature. The reaction mixture was then cooled and then diluted with ethyl acetate. It was washed once with a 0.5N NaOH solution, once with brine and then dried ($Na_2SO_4$). The mixture was filtered and the solvent was removed via vacuum. The resulting product was chromatographed on silica gel (eluted with 50% ethyl acetate in hexane) to give the compound of Formula 19.0, 2.2 g, as an off-white solid.

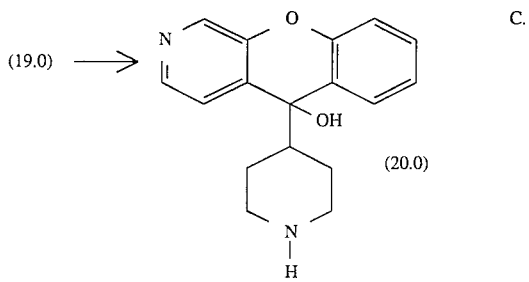

C.

To a solution of the compound of Formula 19.0 (1.01 g) in ethanol (30 mL) was added a solution of KOH (1.5 g) in water (30 mL). The reaction mixture was refluxed for 21 hours. After cooling, it was diluted with $CH_2Cl_2$, washed with water and then dried ($Na_2SO_4$). The mixture was then filtered and the solvent was removed with vacuum on a rotory evaporator to give the compound of Formula 20.0, 0.643 g, m.p. 233°–236° C.

PREPARATIVE EXAMPLE 4

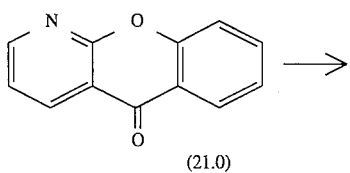
(21.0)

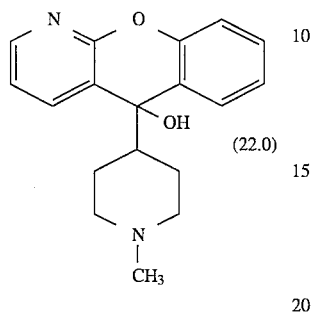
(22.0)

The compound of Formula 22.0 was obtained when the compound of Formula 21.0 was used in a procedure similar to that described in Step A of Preparative Example 3.

B.

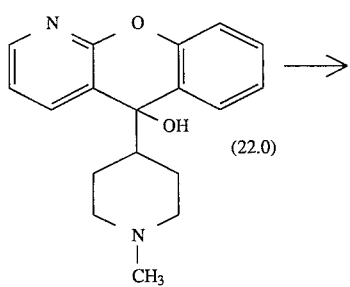
(22.0)

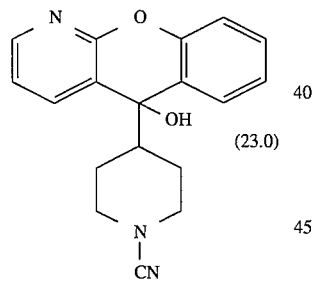
(23.0)

To a solution of BrCN (12.4 g) in CH₂Cl₂ (50 mL) was added a compound of Formula 22.0 (20.0 g in 200 mL of methylene chloride). The reaction mixture was stirred overnight at room temperature and then washed with 10% HCl solution. The acidic aqueous layer was separated and then basified with 50% NaOH solution. The basified aqueous layer was extracted with CHCl₃, dried (MgSO₄), filtered and the solvent was removed to give 11.3 g (solids) of Formula 23.0.

A.

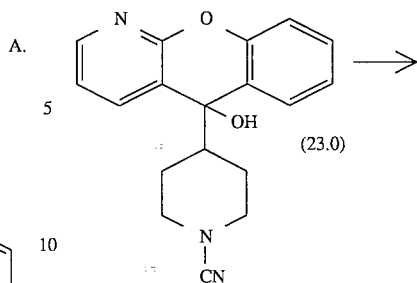
(23.0)

C.

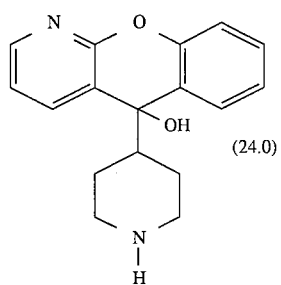
(24.0)

The compound of Formula 24.0 was obtained by using the compound of Formula 23.0 in a procedure similar to that described in Step C of Preparative Example 3.

EXAMPLE 1

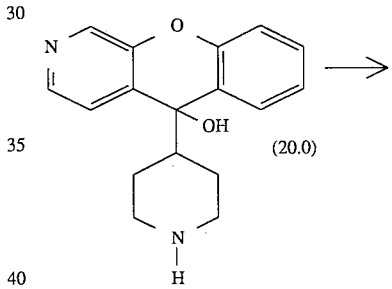
(20.0)

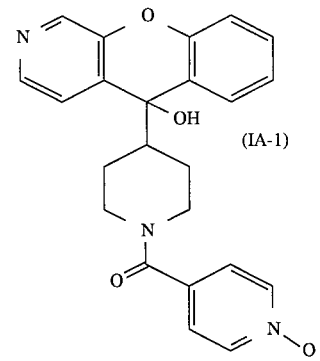
(IA-1)

To a mixture of 190 mg (0.68 mmol) of the compound of Formula 20.0 and 113 mg (0.81 mmol) of isonicotinic acid N-oxide in 25 mL of dry methylene chloride at ice bath temperature, and under an argon atmosphere, was added 197 mg (1.02 mmol) of DEC and 138 mg (1.02 mmol) of HOBT. The ice bath was removed after 15 minutes and the reaction mixture was allowed to stir for 3 hours at room temperature. The reaction mixture was diluted with methylene chloride and washed once with aqueous NaHCO$_3$ (0.5M) and once with brine and then dried with Na$_2$SO$_4$. This mixture was then filtered and the solvent was removed under vacuum.

The product was purified via a flash silica gel (230–440 mesh) column, eluting with 5% methanol saturated with ammonia in methylene chloride to give 147 mg of the compound of Formula IA-1 as white solids: m.p. 249°–250° C., MS (FAB) M/Z 404 (M$^+$+1).

In a similar manner, the compounds of Table 3 below were prepared utilizing the indicated starting material.

TABLE 3

| EX No. | Starting Material | Final Product | Physical Data |
|---|---|---|---|
| 2 | | (IA-2) | MS (FAB) M/Z 403 (M$^+$+1) |
| 3 | | (IA-3) | MS (FAB) M/Z 404 (M$^+$+1) |
| 4 | | (IA-4) | m.p. 230–233° C.; MS (FAB) M/Z 404 (M$^+$+1) |

TABLE 3-continued

| EX No. | Starting Material | Final Product | Physical Data |
|---|---|---|---|
| 5 | (structure with N-CH3 acridine, OH, piperidine-NH) | (IA-5) | MS (FAB) M/Z 416 (M+ + 1) |
| 6 | (structure with S-bridged tricyclic, OH, piperidine-NH) | (IA-6) | MS (FAB) M/Z 419 (M+ + 1) |
| 7 | (structure with chloro tricyclic pyridine, OH, piperidine-NH) | (IA-7) | MS (FAB) M/Z 450 (M+ + 1) |
| 8 | (structure with tricyclic pyridine, OH, piperidine-NH) | (IA-8) | MS (FAB) M/Z 416 (M+ + 1) |

EXAMPLE 9

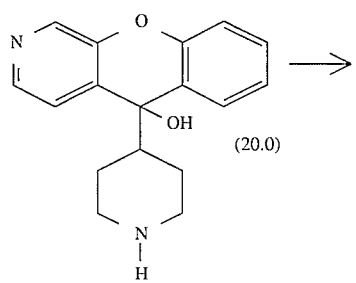

To a solution of carbontetrabromide (319 mg, 0.96 mmol) and 4-pyridylcarbinol N-oxide (119 mg, 0.96 mmol) in 10 mL of methylene chloride at room temperature was added triphenylphosphine, 252 mg (0.96 mmol). This mixture was stirred at room temperature for one hour, and then 160 mg (0.57 mmol) of the compound of Formula 20.0 was added followed by addition of 0.134 mL (0.96 mmol) of triethylamine. The reaction mixture was stirred at ambient temperature and under argon for two hours. It was then diluted with 300 mL of methylene chloride and then washed once with aqueous $K_2CO_3$ (0.5M), once with brine and then dried with $Na_2SO_4$. After filtration the solvent was removed under vacuum and the crude product was chromatographed with silica gel (230–400 mesh), eluting with 5% methanol saturated with ammonia in $CH_2Cl_2$ to give 167 mg of the compound of Formula IA-9 as an off-white glassy solid. MS (FAB) M/Z 390 ($M^+$+1).

In a similar manner, the compounds of Table 4 below were prepared utilizing the indicated starting material.

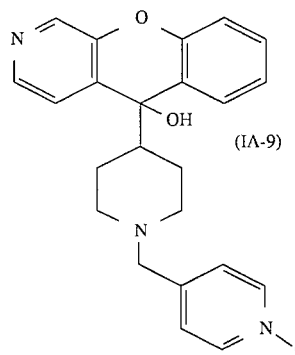

TABLE 4

| EX No. | Starting Material | Final Product | Physical Data |
|---|---|---|---|
| 10 | | | MS (FAB) M/Z 389 ($M^+$ + 1) |
| 11 | | | MS (FAB) M/Z 390 ($M^+$ + 1) |

TABLE 4-continued

| EX No. | Starting Material | Final Product | Physical Data |
|---|---|---|---|
| 12 | (structure) | (IA-12) | m.p. 201–203° C.; MS (FAB) M/Z 390 (M⁺ + 1) |
| 13 | (structure) | (IA-13) | MS (FAB) M/Z 402 (M⁺ + 1) |
| 14 | (structure) | (IA-14) | MS (FAB) M/Z 405 (M⁺ + 1) |

The following are examples of pharmaceutical dosage forms which contain a compound of the invention. As used therein, the term "active compound" is used to designate the compound

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

The scope of the invention in its pharmaceutical composition aspect is not to be limited by the examples provided, since any other compound of Formula I can be substituted into the pharmaceutical composition examples.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |

-continued

| No. | Ingredients | mg/tablet | mg/tablet |
|---|---|---|---|
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of Formula I:

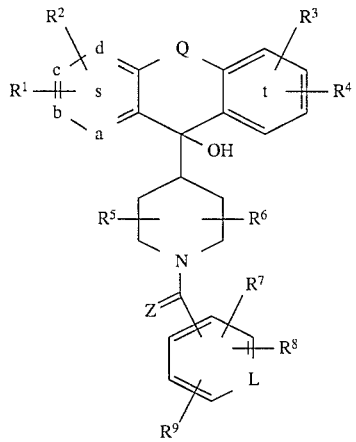

or a pharmaceutically acceptable salt or solvate thereof, wherein one of a, b, c, and d represents N or NO and the remaining a, b, c, and d are carbon atoms; or all of a, b, c, and d represent carbon atoms;

L represents N or $N^+O^-$;

Q is selected from the group consisting of: —O—, and —S—;

$R^1$, $R^2$, $R^3$, and $R^4$ are each independently selected from the group consisting of: H, halo, —$CF_3$, —$OR^{11}$, —$C(O)R^{11}$, —$SR^{11}$, —$S(O)_eR^{12}$ wherein e is 1 or 2, —$N(R^{11})_2$, —$NO_2$, —$OC(O)R^{11}$, —$CO_2R^{11}$, —$OCO_2R^{12}$, —$CON(R^{11})_2$, —$NR^{11}C(=O)R^{11}$, —CN, alkyl, aryl, alkenyl and alkynyl, said alkyl group is optionally substituted with —$OR^{11}$, —$SR^{11}$, —$N(R^{11})_2$ or —$CO_2R^{11}$, and said alkenyl group is optionally substituted with halo, —$OR^{12}$ or —$CO_2R^{11}$;

adjacent $R^1$ and $R^2$ groups can optionally be taken together to form a benzene ring fused to the ring s;

adjacent $R^3$ and $R^4$ groups can optionally be taken together to form a benzene ring fused to the ring t;

$R^5$ and $R^6$ are each independently selected from the group consisting of: H, alkyl and aryl; or $R^5$ can be taken together with $R^6$ to represent =O or =S;

$R^7$, $R^8$ and $R^9$ are each independently selected from the group consisting of: H, halo, —$CF_3$, —$OR^{11}$, —$C(O)R^{11}$, —$SR^{11}$, —$S(O)_eR^{12}$ wherein e is 1 or 2, —$N(R^{11})_2$, —$NO_2$, —CN, —$CO_2R^{11}$, —$OCO_2R^{12}$, —$OC(O)R^{11}$, —$CON(R^{11})_2$, —$NR^{11}C(O)R^{11}$, alkyl, aryl, alkenyl and alkynyl, said alkyl group is optionally substituted with —$OR^{11}$, —$SR^{11}$, —$N(R^{11})_2$, or —$CO_2R^{11}$, and said alkenyl group is optionally substituted with halo, —$OR^{12}$ or —$CO_2R^{11}$;

$R^{10}$ is selected from the group consisting of: H and alkyl;

$R^{11}$ is selected from the group consisting of: H, alkyl and aryl;

$R^{12}$ is selected from the group consisting of: alkyl and aryl; and

Z is selected from the group consisting of: O and S, or Z optionally represents H and $R^{10}$.

2. The compound of claim 1 wherein L represents $N^+O^-$.

3. The compound of claim 2 wherein Z is selected from the group consisting of O, and (H and $R^{10}$) wherein $R^{10}$ is H.

4. The compound of claim 3 wherein $R^1$, $R^2$, $R^3$, and $R^4$ are each independently selected from the group consisting of: H, halo, —$OR^{11}$, and alkyl.

5. The compound of claim 4 wherein $R^5$ and $R^6$ are each hydrogen.

6. The compound of claim 5 wherein $R^7$, $R^8$, and $R^9$ are each independently selected from the group consisting of: H, halo, —$OR^{11}$, and alkyl.

7. The compound of claim 6 wherein $R^1$, $R^2$, $R^3$, $R^4$, $R^7$, $R^8$, and $R^9$ are selected from the group consisting of H and Cl.

8. The compound of claim 7 having the Formula IA:
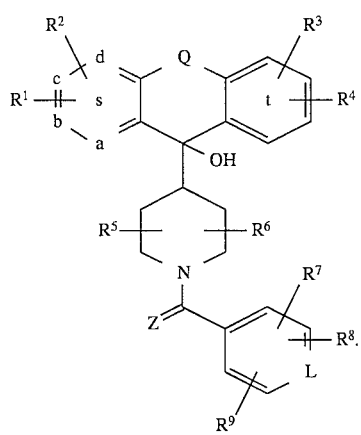
(IA)
9. The compound of claim 8 wherein one of a, b, c, or d is nitrogen and the remaining a, b, c, or d are carbon atoms.
10. The compound of claim 8 wherein a, b, c, and d represent carbon atoms.
11. The compound of claim 1 having a formula selected from the group of formulas consisting of:
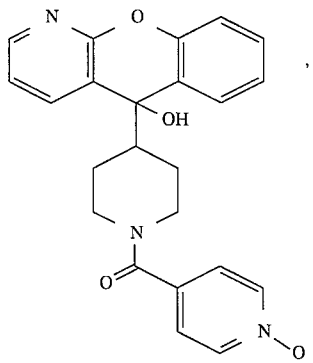
(IA-1),
(IA-2),
(IA-3),
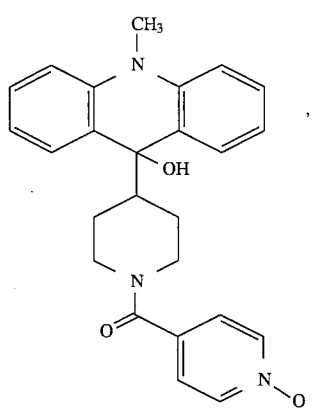
(IA-4),
(IA-5),
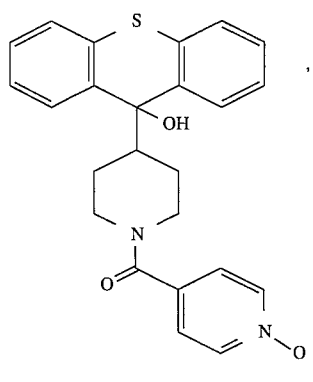
(IA-6),
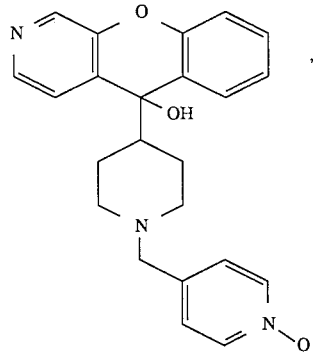
(IA-9)

(IA-10)

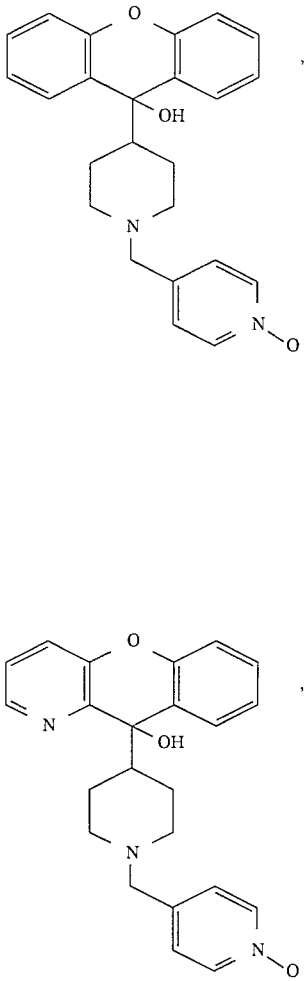

(IA-11)

(IA-12)

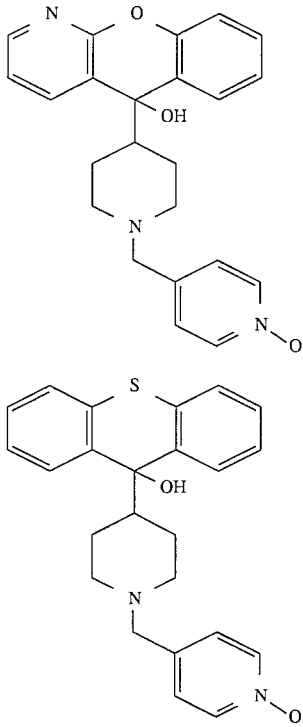

(IA-14)

12. A pharmaceutical composition comprising an effective amount of a compound of claim 1 in combination with a pharmaceutically acceptable carrier.

13. A method of treating asthma comprising administering to a mammal in need of such treatment an anti-asthmatic effective amount of a compound of claim 1.

14. A method of treating inflammation comprising administering to a mammal in need of such treatment an anti-inflammatory effective amount of a compound of claim 1.

15. A method of treating allergy comprising administering to a mammal in need of such treatment an anti-allergic effective amount of a compound of claim 1.

* * * * *